United States Patent [19]

Knifton

[11] Patent Number: 5,214,217
[45] Date of Patent: May 25, 1993

[54] METHOD FOR ONE-STEP SYNTHESIS OF METHYL T-BUTYL ETHER

[75] Inventor: John F. Knifton, Austin, Tex.

[73] Assignee: Texaco Chemical Company, White Plains, N.Y.

[21] Appl. No.: 917,218

[22] Filed: Jul. 22, 1992

Related U.S. Application Data

[63] Continuation-in-part of Ser. No. 494,281, Mar. 16, 1990, abandoned.

[51] Int. Cl.$^5$ .................... C07C 41/00; C07C 43/04
[52] U.S. Cl. ........................................... 568/618
[58] Field of Search .................... 568/618, 698, 689

[56] References Cited

U.S. PATENT DOCUMENTS

| | | | |
|---|---|---|---|
| 2,282,469 | 5/1942 | Frolich | 568/698 |
| 4,058,576 | 11/1977 | Chanh et al. | 568/698 |
| 4,337,366 | 6/1982 | Fottore et al. | 568/698 |
| 4,886,918 | 12/1989 | Sorensen et al. | 568/698 |

FOREIGN PATENT DOCUMENTS 0007432 1/1982 Japan ........................ 568/698

*Primary Examiner*—Werren B. Lone
*Attorney, Agent, or Firm*—James L. Bailey; Kenneth R. Priem; Cynthia L. Kendrick

[57] ABSTRACT

A method is disclosed wherein t-butanol is reacted with methanol in a reaction zone in the presence of a catalyst to provide methyl-tert-butyl ether and the improvement of accomplishing the reaction in one-step which comprises:

a. using a catalyst selected from the group consisting of acidic aluminas, and crystalline aluminosilicate faujasite-type zeolites, particularly dealuminized Y-type zeolites;

b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl-tert-butyl product.

1 Claim, No Drawings

METHOD FOR ONE-STEP SYNTHESIS OF METHYL T-BUTYL ETHER

CROSS-REFERENCE

This application is a continuation-in-part of U.S. Ser. No. 07/494,281 filed Mar. 16, 1990 abandoned.

This invention concerns an improved process for preparing methyl tertiary butyl ether by the reaction of tertiary butanol and methanol in the presence of a catalyst containing alumina or crystalline aluminosilicate zeolites, particularly super-acid aluminas and faujasite-type zeolites. The invention is particularly advantageous in that the reaction takes place in one-step, the catalyst exhibits excellent selectivity to the desired ether product and high levels of tert-butanol conversion are achieved.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether (MTBE) are based upon the liquid-phase reaction of isobutylene and methanol (Eq. 1), catalyzed by a cationic ion-exchange resin (see, for example: Hydrocarbon Processing, October 1984, p. 63; Oil and Gas J., Jan. 1, 1979, p. 76; Chem. Economics Handbook-SRI, September 1986, p. 543–7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

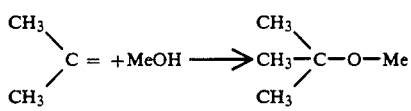  (Eq. 1)

With the expanding use of MTBE as an acceptable gasoline additive, however, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

It does not appear that any in the art have used the crystalline aluminosilicate faujasite group of zeolites as catalysts for the selective synthesis of methyl tertiary butyl ether from tertiary butyl alcohol and methanol.

It would be a substantial advance in the art if methyl tertiary butyl ether could be selectively synthesized from tertiary butyl alcohol and methanol in one step using a faujasite, particularly a Y-type, zeolite which allows for rapid conversion of t-butanol. The accompanying examples demonstrate a significant improvement in yield of MTBE when using the zeolites of the instant invention for such a reaction.

SUMMARY OF THE INVENTION

In accordance with certain of its aspects, the novel method of this invention for preparing methyl tert-butyl ether from tertiary butyl alcohol (t-butanol) and methanol in one-step comprises reacting tertiary butyl alcohol and methanol in the presence of a catalyst comprising an alumina, or crystalline aluminosilicate zeolite at an elevated temperature and moderate pressure. Examples demonstrate the effectiveness of super acid aluminas and faujasite-type zeolites.

DESCRIPTION OF THE INVENTION

Preparation of the product of this invention may be carried out typically by reacting tertiary butyl alcohol and methanol in the presence of an etherification catalyst. The etherification is carried out in one step and the catalyst preferably comprises an acidic alumina, or a crystalline aluminosilicate zeolite, but particularly a faujasite-type zeolite or a super acid alumina.

The reaction can be represented by the following:

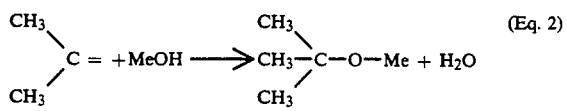

$$\begin{array}{c}CH_3\\ \diagdown\\ C = +MeOH \longrightarrow CH_3-C-O-Me + H_2O\\ \diagup\\ CH_3\end{array} \quad \begin{array}{c}CH_3\\ \diagdown\\ \\ \diagup\\ CH_3\end{array} \quad (Eq. 2)$$

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

The same process may also be applied to the preparation of other alkyl tertiary alkyl ethers. For example, said process may be applied to the reaction of a $C_1$-$C_6$ primary alcohol such as methanol, ethanol, n-propanol and n-hexanol with a $C_4$-$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$-$C_5$ alcohols, could be reacted to give a mixture of alkyl tert-alkyl ethers.

The catalysts used to effect this reaction are aluminas or crystalline aluminosilicate zeolites, but particularly acidic, faujasite-type zeolites and super acid aluminas.

While a variety of alumina catalysts may be effective in the subject reaction (Eq. 2), it is necessary only that the alumina be acidic under normal operating conditions. The acidic sites on the solid alumina matrix may be either Lewis or Bronsted acid sites, or combinations thereof. The alumina may take many different forms, it may be an $\alpha$-alumina, a $\beta$-alumina, or any type of $\gamma$-alumina, including transitional forms (see Industrial Alumina Chemicals, by C. Misra, ACS Monogram 184). The identification of surface acidity of such aluminas may be confirmed by titration with amine base, e.g. ammonia, n-butylamine, etc.

Said aluminas may or may not contain impurities, such as the alkali metals, e.g. sodium or potassium, or alkaline earth metals such as calcium.

The preferred alumina catalysts are 'super' acid aluminas, that are generated by treatment of said aluminas with mineral acids, such as sulfuric acid and phosphoric acid, and which are believed to contain both Bronsted and Lewis acid sites, and which have a surface area of greater than 10 $m^2/g$ especially >100 $m^2/g$. Such super acid aluminas should have a titratable acidity of at least 0.05 meq/g include the super acid aluminas marketed by Harshaw-Filtrol Partnership, such as Harshaw-Filtrol Super Aluminas Al-3998, and Al-4198. These super acid aluminas have a greater proportion of Bronsted-acid-to-Lewis acid sites on the available surface than are normally found with standard aluminas. Their titratable acidities are 0.09 and 0.12 meq/g respectively.

Good results were also realized with certain crystalline aluminosilicate zeolites, particularly the isostructural group of faujasite zeolites that include the synthetic X and Y zeolites, the rare mineral faujasite and a number of other synthetic zeolites (see D. W. Beck, 'Zeolite Molecular Sieves', Willey Interscience, 1974). The unit cells of faujasite and zeolites X and Y are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of chargebalancing cations. These are exclusively sodium ions in zeolites X and Y in their synthesized form and a complex distribution between sodium, potassium, magnesium and calcium in naturally-occurring faujasite. Typical cell contents for the three zeolites in the hydrated form are:

| | |
|---|---|
| faujasite | $(Na_2,K_2,Mg,Ca)_{29.5}[(AlO_2)_{59}(SiO_2)_{133}],235H_2O$ |
| zeolite X | $Na_{86}[(AlO_2)_{86}(SiO_2)_{106}],264H_2O$ |
| zeolite Y | $Na_{56}[(AlO_2)_{56}(SiO_2)_{136}],250H_2O$ |

Zeolites X and Y are distinguished on the basis of the relative concentration of silicon and aluminum atoms and the consequent effects on detailed structure and related chemical and physical properties. The aluminum atoms in the unit cell of zeolite X vary from 96 to 77 giving a Si:Al ratio between 1 and 1.5, whereas for zeolite Y they vary from 76 to 48 giving a Si:Al ratio between 1.5 and 3.0. It follows that both the cation concentration and charge density on the alumino-silicate structure are higher for X zeolite than for Y zeolite.

The feature which determines the difference between faujasites and other zeolites built up from sodalite units is the double 6-membered ring or hexagonal prism, by which the units are linked. The sodalite unit, or $\beta$-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the $\beta$-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed $\alpha$-cages, or supercages. The $\alpha$-cage is a 26-hedron with a free diameter of $\approx 1.3$ nm, and it can be entered through four distorted 12-member rings of diameter 0.80–0.90 nm. In this way each $\alpha$-cage is tetrahedrally joined to four others giving a complex system of void space extending throughout the zeolite structure The $\alpha$- and $\beta$-cages together give X and Y zeolites the largest void volume of any known zeolite, which is ca. 50 vol % of the dehydrated crystal. From the catalytic viewpoint, however, the $\alpha$-cages are by far the most important, since, unlike the $\beta$-cages, they permit entry of numerous aliphatic and aromatic compounds.

Particularly effective in the subject synthesis of MTBE are the synthetic Y-zeolites. Preferably said zeolites should be in a strongly acidic form whereby some, or all, of the cations (Group I or II, alkali or alkaline earth metal ions such as sodium, potassium, calcium or magnesium) is exchanged by protons either through ammonium exchange followed by thermal stabilization (deammoniation, removal of $NH_3$) at elevated temperatures (e.g. 400°–500° C.) through mineral acid treatment, etc. Alternatively, said Y-zeolites may be dealuminized by hydrothermal treatment, by mineral acid treatment or by treatment with ethylenediaminetetraacetic acid (EDTA) or other chelating agents, in which case said dealuminized Y-zeolites should have a Si:Al ratio of greater than three. A further possibility is that said Y-zeolites may be rare-earth exchanged with, for example, a mixture of rare-earth salts, by treatment with lanthanum salts, etc. Said rare-earth exchanged Y-zeolites would then have a Si:Al ratio of 1.5 to 3. The exchange of the sodium ions of the Y-zeolite by rare earth, ammonium or alkylammonium ions has been reviewed (see, for example, R. Rudham and A. Stockwell, The Chemical Society Specialist Periodical Report - Catalysis, Vol. I, 1977, Chapter 3).

A further possibility is the use of Y-zeolites in the subject application that have been modified by transition-metal exchange or impregnation, in particular, the use of Y-zeolites that have been modified by exchange of sodium ions etc., or by impregnation, of Group VIII metal salts such as those of cobalt(II) and nickel(II). Both methods are discussed in detail in an article by J. W. Ward, Applied Industrial Catalysis, Vol. 3, p. 271 (1984). For the nickel-treated Y-zeolites, useful in MTBE service from methanol and t-butanol (Eq. 2), the nickel content may range up to 10 wt %.

Said Y-zeolites, or modified Y-zeolites, may be employed alone, or to ensure greater physical strength and stability when in the form of extrudates, pellets, or granules, etc., they may also be used in the presence of certain binders. Suitable binders in the MTBE application include silica-alumina binders, alumina binders and carbon binders, etc.

Illustrating of suitable zeolites for the one-step synthesis of MTBE from methanol plus t-butanol include typical Y-type zeolites, particularly the acidic, dealuminized Y-zeolites, such as Zeochem's Z6-06-02 having a bulk Si:Al ratio of ca. 5.3–5.4, and Zeochem's zeolite-Y, L-2585 having a Si:Al ratio of ca. 5.5 or greater, ammonium-exchanged, thermally-stabilized Y-zeolites such as PQ Corporation's CP 304-37, having a Si:Al ratio of ca. 11:1, rare-earth exchanged zeolites such as the Linde SK-500 extrudates, having a Si:Al ratio of between 1.5:1 and 2:1, as well as transition-metal treated zeolites, particularly nickel-treated Y-zeolites, illustrated by Zeocat Ni Z6-06-02, having 7.4 % Ni on Y-zeolite.

The performance of such zeolites in MTBE synthesis from t-butanol and methanol in one-step (Eq. 2) is illustrated by the accompanying examples.

Said catalysts may be in the form of powders, pellets, granules, spheres, shapes and extrudates. The examples described herein demonstrate the advantages of using powders and extrudates. Extrudates which work well include Y-zeolite extrudates of high acidity and surface areas of $>100$ m$^2$/g, such as (#Z6-06-02) from Zeochem having a surface area of 450 m$^2$/g. Another zeolite, used in Example II is a thermally dealuminized Y-zeolite from Zeochem Company, a powder with a surface area of ca. 400 m$^2$/g.

A super acid alumina was used in Example III which has a high pore volume (#583A-22-16.6) from Harshaw, E-⅛" extrudate with a surface area of 190 m$^2$/g. Also used in Example IV was #583A-22-15-9, a super acid alumina from Harshaw with E-⅛" and surface of 175 m$^2$/g.

As will be demonstrated by the examples, these catalysts are preferably of high purity and high surface area. It has been found in the process of this invention that greater conversion of tertiary butanol and methanol is achieved where the surface area of the support catalyst is generally $>10$ m$^2$g.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 180° C. The total operating pressure may be from 0 to 1000 psig, or higher. The preferred pressure range is 50 to 500 psig.

Typically, MTBE is generated continuously in up to ca. 38 wt % concentration in the crude liquid product at total liquid hourly space velocities (LHSV) of up to 4 and relatively mild conditions, where:

$$LHSV = \frac{\text{Volume Of Total Liquid Feed Run Through The Reactor Per Hour}}{\text{Volume of Catalyst In Reactor}}$$

The examples which follow illustrate the one-step synthesis of MTBE from TBA and MeOH (Eq. 2) using zeolites and aluminas, particularly Y-type zeolites and high acid aluminas in the form of high surface area powders and extrudates. The examples are only intended as a means of illustration and it is understood the invention is not meant to be limited thereby.

Conversions of t-butanol (TBA, wt %) are estimated in the following examples using the equation:

$$\frac{\left(\begin{array}{c}\text{Wt \% Conc. of} \\ \text{TBA in Feed}\end{array} - \begin{array}{c}\text{Wt \% Conc. of} \\ \text{TBA in Product}\end{array}\right)}{\text{Wt \% Conc. of TBA in Feed}} \times 100$$

$$\frac{\text{Moles of MTBE in Product Liquid}}{\text{moles of TBA converted}} \times 100$$

Of particular note:

a) The rare-earth exchanged and thermally-stabilized, ammonium exchanged Y-zeolites provide $>70\%$ TBA conversion per pass at 140°–160° C. operating temperatures in Example 1, VI and VII.

b) Product phase separation into an isobutylene-MTBE rich phase and an aqueous methanol heavier phase is illustrated in Examples VIII and IX with the rare-earth exchanged and thermally-stabilized, ammonium-exchanged Y-zeolites.

EXAMPLE 1

This example illustrates the co-synthesis of methyl t-butyl ether from t-butanol and methanol using a particular aluminosilicate Y-type zeolite catalyst.

The synthesis was conducted in a tubular reactor (⅜" id; 12" long), constructed of 316 stainless steel, operated upflow and mounted in a furnace, controllable to ±1.0° C and fitted with pumps allowing flow control to $<\pm$ cc/hr. The reactor was also fitted with a pressure regulating device and equipment for monitoring temperature, pressure and flow rate.

The reactor was charged at the beginning of the experiment with 25 cc of Zeochem Y-zeolite 1/16" extrudates (#Z6-06-02). A screen of glass beads was placed at the top and bottom of the reactor to ensure the zeolite would remain in the middle portion.

The catalyst bed was first conditioned overnight by washing with methanol/t-butanol (2:1 molar mix) at 100° C., 300 psi back pressure and a liquid flow rate of 25 cc/hr. The same solution of methanol (1281.6 g, 40.0 mole) plus t-butanol (1482.4 g), (20.0 mole) was then pumped through the catalyst bed at 25 cc/hr, While the reactor was held at 100° C., at total pressure of 300 psi. Samples of product were taken periodically either by trapping in a dry ice cooled container, or by collecting on-stream (on-line) in a 316 ss bomb. Typical analyses data for samples taken under these conditions are summarized in Table I. Catalyst performance at other operating temperatures and liquid flow rates was also measured, after reaching equilibrium conditions overnight. Summary data for these runs are also given in Table I.

Here it may be noted that United Catalysts Y-Zeolite, Z6-06-02, gave MTBE in ca. 39% concentration when run at LHSV of 1 (e.g. Sample #17) and ca. 34% concentration in the crude liquid product when run at LHSV of 4 (e.g. Sample #22). The operating conditions in both cases (140° C., 300 psi) are moderate. This catalyst was screened over the temperature range of 100°–140° C. At 140° C., LHSV =4, Sample #22 shows:

```
Estimated TBA conversion per pass = 71%
MTBE yield (basis TBA converted) = 73 mole %.
```

EXAMPLES II TO V

Using the procedures and analyses methods of Example I, these examples illustrate the one-step synthesis of MTBE from methanol plus t-butanol (2:1 molar mix) over a range of operating temperatures and space velocities, but with the following catalysts (25 cc each):

A dealuminized Y-zeolite from Zeochem, L-2585, in powder form with no binder.

A high pore volume, super acid alumina, Al-4198, from Harshaw/Filtrol, in extruded form (⅛" diameter).

c) A second super acid alumina, Al-3998, from Harshaw/Filtrol, also in extruded form (⅛" diameter).

d) A 7.4% nickel-on-Y-zeolite catalyst from Zeochem, as extrudates.

The results are summarized in Tables I to III. Of Note:

In Example II, dealuminized Y-Zeolite from Zeochem gave MTBE in ca. 28% concentration when run at LHSV of 1 (e.g. Sample #15) and ca. 24% concentration in the crude liquid product when run at LHSV of 4 (e.g. Sample #27). The screening conditions in this series of runs were 100°–160° C., 300 psi. At 160° C., LHSV =4, Sample #27 shows:

```
Estimated TBA conversion per pass = 56%
MTBE yield (basis TBA converted) = 68 mole %.
```

In the runs in Examples III and IV, two super-acid aluminas from Harshaw were evaluated for MTBE production. At 180° C., Sample #23 shows ca. 20% concentration of MTBE in the crude liquid product. A similar result was obtained at the same conditions (180° C., 300 psi, LHSV =1) with the second super-acid alumina catalysts (see Sample #32).

EXAMPLES VI AND VII

Using the procedures and analyses methods of Example I, these two examples illustrate the one-step synthesis of MTBE from methanol plus t-butanol (1.1:1 molar mix) with the following catalysts (25 cc each):

a) A rare-earth exchanged Y-zeolite having a Si:Al ratio of 1.5 →2 and 10–20% alumina binder, Linde SK-500, in 1/16" diameter extruded form.

b) A thermally-stabilized, ammonium exchanged, Y-zeolite having a Si:Al ratio of ca. 11:1 with 80% silica-alumina binder ($SiO_2$:$Al_2O_3$ ratio 16.84), from PQ Corporation, CP304-37, in extruded form.

The results are summarized in Tables IV and V. Of note:

In Example VI, the rare-earth exchanged Y-zeolite performed well over 10 days of operation at 160° C., LHSV=2 for Sample #3:

```
Estimated TBA conversion per pass =    74%
MTBE yield (basis TBA converted) =     42 mole %
Isobutylene yield (basis TBA converted) = 59 mole %
Total MTBE + isobutylene yield =       101 mole %
```

In Example VII, the thermally-stabilized, ammonium-exchanged Y-zeolite performed well over a range of operating temperatures (100°–180° C.) and flow rates (50–125 cc/hr, LHSV =2→5). For Samples 6 and 7, taken at 140° and 160° C., respectively, the results are as follows:

|  | SAMPLE #6 (140° C.) | SAMPLE #7 (160° C.) |
|---|---|---|
| Estimated TBA conversion per pass = | 72 | 81 |
| MTBE yield (basis TBA converted) = | 62 | 39 |
| Isobutylene yield (basis TBA converted) = | 35 | 64 |

EXAMPLE VIII

This example also illustrates the performance of a rare-earth exchanged Y-zeolite in the production of methyl t-butyl ether from t-butanol and methanol over a range of conditions.

Using a tubular reactor (½" i.d., 12" long), constructed of 316 stainless steel, operated upflow and mounted in a furnace controllable to ±1.0° C. and fitted with pumps allowing flow to <±1 cc/hr. The reactor was also fitted with a pressure regulating device and equipment for monitoring temperature, pressure and flow rate. 25 cc of Y-zeolite (Linde SK-500, 1/16" diameter extrudates) was charged to the reactor system and performance was monitored over a range of operating temperatures (100–180° C.) and flow rates (50–160 cc/hr). The results are summarized in Table VI.

Calculated tBA conversion and C₄H₈/MTBE selectivities at 140° and 160° C. are typically as follows:

| Sample | Operating Temp (°C.) | TBA Conv. (%) | Molar Selectivity (%) C₄H₈ | MTBE |
|---|---|---|---|---|
| 6 | 140 | 56 | 35 | 64 |
| 8 | 160 | 78 | 59 | 39 |

Product phase separation into a lighter isobutylene-MTBE rich phase and a heavier aqueous methanol phase is evident at 180° C. operating temperature (see Samples 9 and 10).

EXAMPLE IX

This example also illustrates the performance of a dealuminized Y-zeolite in the production of methyl t-butanol and methanol.

Using the equipment and procedures of Example VIII, 25 cc of Y-zeolite (CP-304-37, 1/16″ extrudates) was charged to the reactor system and performance was monitored over a range of operating temperatures (100°–180° C.) and flow rates (50–160 cc/hr). The results are summarized in Table VII.

Calculated tBA conversions and C₄H₈/MTBE selectivities at 140° and 160° C. are typically as follows:

| Sample | Operating Temp (°C.) | TBA Conv. (%) | Molar Selectivity (%) C₄H₈ | MTBE |
|---|---|---|---|---|
| 6 | 140 | 72 | 35 | 62 |
| 7 | 160 | 81 | 64 | 39 |

Product phase separation into a linear isobutylene-MTBE rich phase and a heavier aqueous methanol phase is evident at 180° C. operating temperature (see Samples 9 and 10).

TABLE I

| Ex. | Catalyst | Feed Sample | Flow Rate (cc/hr) | Pressure (psig) | Temp. (°C.) | Sample | MTBE | i-C₄ | MeOH | tBA | H₂O |
|---|---|---|---|---|---|---|---|---|---|---|---|
| | | F | | | | | | | 45.0 | 54.8 | |
| I | Y-Zeolite Z6-06-02 | | 25 | 300 | 100 | #1 | 13.0 | 0.9 | 40.6 | 41.7 | 3.7 |
| | | | | | | #6 | 14.0 | 1.1 | 39.2 | 39.9 | 5.6 |
| | | | | | | #7 | 13.7 | 1.3 | 40.1 | 40.7 | 4.1 |
| | | | 25 | 300 | 120 | #8 | 35.0 | 2.7 | 32.6 | 19.6 | 10.0 |
| | | | | | | #12 | 35.0 | 2.5 | 32.5 | 19.6 | 9.8 |
| | | | 25 | 300 | 140 | #14 | 37.9 | 4.9 | 31.6 | 12.8 | 12.5 |
| | | | | | | #17 | 38.6 | 5.5 | 30.1 | 12.7 | 12.0 |
| | | | 100 | 300 | 140 | #18 | 34.9 | 5.5 | 32.6 | 16.2 | 10.7 |
| | | | | | | #20 | 35.1 | 5.1 | 32.7 | 16.4 | 10.7 |
| | | | | | | #22 | 34.0 | 5.9 | 31.9 | 15.8 | 12.3 |
| | | F | | | | | | | 47.0 | 53.0 | |
| II | Y-Zeolite L-2585 | | 25 | 300 | 100 | #1 | 3.7 | 1.3 | 45.4 | 48.7 | 0.7 |
| | | | | | | #5 | 2.4 | 0.5 | 45.8 | 51.0 | 0.2 |
| | | | 25 | 300 | 120 | #7 | 12.5 | 2.0 | 42.5 | 37.8 | 3.1 |
| | | | | | | #2 | 10.9 | 1.3 | 43.0 | 42.4 | 2.4 |
| | | | | | 125 | #18 | 19.7 | 3.7 | 39.5 | 31.0 | 5.9 |
| | | | 25 | 300 | 140 | #15 | 08.0 | 4.2 | 36.8 | 23.4 | 7.5 |
| | | | | | | #19 | 16.3 | 3.7 | 38.2 | 27.8 | 6.6 |
| | | | | | | #20 | 27.0 | 4.2 | 38.4 | 26.6 | 7.5 |
| | | | 25 | 300 | 160 | #21 | 25.7 | 5.7 | 38.3 | 21.3 | 9.0 |
| | | | | | | #25 | 26.2 | 5.6 | 37.4 | 21.5 | 8.0 |
| | | | | | | #27 | 23.8 | 6.0 | 38.2 | 28.5 | 8.4 |

TABLE II

| Ex. | Catalyst | Feed Sample | Flow Rate (cc/hr) | Pressure (psig) | Temp. (°C.) | Sample | MTBE | i-C₄ | MeOH | tBA | H₂O |
|---|---|---|---|---|---|---|---|---|---|---|---|
| | | F | | | | | | | 46.9 | 52.8 | |
| III | Super Acid Alumina | | 25 | 300 | 100 | #1 | 1.8 | 0.2 | 46.9 | 50.3 | 0.6 |
| | | | | | | #6 | 2.2 | 0.1 | 43.9 | 48.1 | 0.2 |
| | | | | | | #7 | 1.2 | 0.2 | 46.8 | 51.7 | — |
| | | | 25 | 300 | 120 | #8 | 1.6 | 0.2 | 46.3 | 51.6 | 0.3 |
| | | | | | | #12 | 2.0 | 0.3 | 46.8 | 50.5 | 0.3 |
| | | | | | | #14 | 2.1 | 0.3 | 46.2 | 50.2 | 1.1 |
| | | | 25 | 300 | 180 | #16 | 6.6 | 1.3 | 45.2 | 44.8 | 2.1 |
| | | | | | | #19 | 7.7 | 1.7 | 44.4 | 42.9 | 2.5 |
| | | | | | | #20 | 7.6 | 1.9 | 44.1 | 43.6 | 2.6 |
| | | F-1 | | | | | | | 46.8 | 53.0 | |
| | | | 25 | 300 | 180 | #22 | 14.3 | 6.1 | 42.3 | 32.4 | 4.8 |
| | | | | | | #23 | 19.7 | 5.6 | 41.8 | 25.9 | 7.0 |
| IV | Super Acid Alumina | | 25 | 300 | 210 | #25 | 14.5 | 2.5 | 58.1 | 3.3 | 21.3 |
| | | | | | | #29 | 15.9 | 2.6 | 57.3 | 3.1 | 20.8 |
| | | | 25 | 300 | 180 | #31 | 17.5 | 6.1 | 42.3 | 28.3 | 5.6 |
| | | | | | | #32 | 19.8 | 5.3 | 41.6 | 25.5 | 7.7 |

TABLE III

| Ex. | Catalyst | Feed Sample | Flow Rate (cc/hr) | Pressure (psig) | Temp. (°C.) | Sample | MTBE | i-C$_4$ | MeOH | tBA | H$_2$O |
|---|---|---|---|---|---|---|---|---|---|---|---|
| V | Ni-Zeolite | F | | | | | | | 46.2 | 53.7 | |
| | | | 25 | 300 | 120 | #1 | 0.6 | 0.1 | 46.2 | 52.9 | 0.1 |
| | | | | | | #5 | 0.6 | 0.1 | 46.4 | 52.8 | 0.1 |
| | | | | | | #6 | 0.8 | — | 46.3 | 52.7 | — |
| | | | 25 | 300 | 150 | #9 | 4.4 | 1.1 | 45.3 | 48.1 | 0.9 |
| | | | | | | #11 | 4.2 | 1.2 | 45.2 | 48.4 | 1.0 |
| | | | | | | #12 | 4.2 | 1.3 | 45.3 | 48.6 | 0.6 |
| | | | 25 | 300 | 180 | #15 | 22.5 | 6.0 | 39.8 | 25.0 | 6.8 |
| | | | | | | #16 | 22.4 | 6.4 | 39.6 | 24.5 | 7.0 |

TABLE IV

| Ex. | Catalyst | MeOH/TBA Molar Ratio | Temp. (°C.) | Feed Rate (cc/hr) | Time On Stream (Days) | SAMPLE | H$_2$O | MeOH | C$_4$H$_8$ | TBA | MTBE |
|---|---|---|---|---|---|---|---|---|---|---|---|
| VI | SK-500 | 1.1 | 160 | 50 | | FS | | 29.6 | | 70.0 | |
| | | | | | 2 | 1 | 7.7 | 17.6 | 33.1 | 12.2 | 28.6 |
| | | | | | 3 | 2 | 6.9 | 17.4 | 34.9 | 11.8 | 28.5 |
| | | | | | 6 | 3 | 11.3 | 21.4 | 22.8 | 18.5 | 25.9 |
| | | | | | 8 | 4 | 10.8 | 21.7 | 20.4 | 21.2 | 25.9 |
| | | | | | 10 | 5 | 10.8 | 21.4 | 19.3 | 22.0 | 26.4 |

TABLE V

| Ex. | Catalyst | MeOH/TBA Molar Ratio | Temp. (°C.) | Feed Rate (cc/hr) | Time On Stream (Days) | SAMPLE | H$_2$O | MeOH | C$_4$H$_8$ | TBA | MTBE |
|---|---|---|---|---|---|---|---|---|---|---|---|
| VII | CP304-37 | | | | | F | | | | | |
| | | 1.1:1 | 100 | 50 | 2 | 1 | 2.7 | 26.7 | 3.1 | 54.2 | 13.2 |
| | | | | | | 2 | 3.3 | 25.4 | 3.3 | 52.3 | 15.7 |
| | | | 120 | 50 | 2 | 3 | 8.2 | 18.7 | 7.7 | 29.8 | 35.5 |
| | | | | | | 4 | 9.6 | 17.8 | 7.7 | 26.4 | 38.4 |
| | | → | 140 | 50 | 3 | 5 | 11.0 | 17.9 | 13.5 | 19.5 | 37.5 |
| | | | | | | 6 | 11.1 | 18.1 | 13.5 | 19.3 | 37.3 |
| | | → | 160 | 50 | 4 | 7 | 10.8 | 20.8 | 28.7 | 13.3 | 26.0 |
| | | | | | | 8 | 8.7 | 19.6 | 29.2 | 13.8 | 28.5 |
| | | | 160 | 125 | 6 | 11 | 7.0 | 23.0 | 10.4 | 36.6 | 22.9 |
| | | | | | | 12 | 7.4 | 23.1 | 10.6 | 35.3 | 23.6 |

TABLE VI

| Ex. | Catalyst | MeOH/TBA Molar Ratio | Temp. (°C.) | Feed Rate (cc/hr) | Time On Stream (Days) | SAMPLE | H$_2$O | MeOH | C$_4$H$_8$ | TBA | MTBE |
|---|---|---|---|---|---|---|---|---|---|---|---|
| VIII | SK-500 | 1.1 | | | | FS | | 31.4 | | 68.2 | |
| | | | 100 | 50 | 1 | 1 | 4.2 | 25.2 | 4.5 | 49.3 | 16.6 |
| | | | | | | 2 | 3.6 | 25.3 | 4.1 | 51.0 | 15.9 |
| | | | 120 | 50 | 2 | 3 | 8.3 | 21.5 | 6.9 | 36.3 | 26.9 |
| | | | | | | 4 | 8.6 | 21.0 | 7.7 | 34.0 | 28.7 |
| | | | 140 | 50 | 3 | 5 | 11.0 | 17.6 | 10.0 | 26.7 | 34.6 |
| | | | | | | →6 | 11.3 | 19.0 | 11.8 | 23.5 | 34.3 |
| | | | 160 | 50 | 4 | 7 | 12.9 | 21.4 | 24.7 | 15.2 | 25.5 |
| | | | | | | →8 | 13.5 | 22.2 | 24.0 | 14.9 | 25.1 |
| | | | 180 | 50 | 5 | 9 | 14.1 | 31.6 | 10.4 | 8.8 | 35.1 |
| | | | | | | | 31.8 | 41.4 | 7.1 | 7.5 | 11.5 |
| | | | | | | 10 | 17.0 | 31.7 | 17.0 | 7.3 | 27.2 |
| | | | | | | | 30.0 | 38.8 | 8.0 | 8.6 | 14.1 |
| | | | 160 | 160 | 6 | 11 | 10.0 | 22.2 | 13.1 | 29.7 | 24.9 |
| | | | | | | 12 | 9.8 | 22.1 | 13.1 | 29.9 | 25.0 |

Phase seperation was observed with Samples 9 and 10.

TABLE VII

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| IX | CP-304-37 | 1.1 | | | | FS | | 30.1 | | 69.6 | |
| | | | 100 | 50 | 1 | 1 | 2.7 | 26.7 | 3.1 | 54.2 | 13.2 |
| | | | | | | 2 | 3.3 | 25.4 | 3.3 | 52.3 | 15.7 |
| | | | 120 | 50 | 2 | 3 | 8.2 | 18.7 | 7.7 | 29.8 | 35.5 |
| | | | | | | 4 | 9.6 | 17.8 | 7.7 | 26.4 | 38.4 |
| | | | 140 | 50 | 3 | 5 | 11.0 | 17.9 | 13.5 | 19.5 | 37.5 |
| | | | | | | →6 | 11.1 | 18.1 | 13.5 | 19.3 | 37.3 |
| | | | 160 | 50 | 4 | →7 | 10.8 | 20.8 | 28.7 | 13.3 | 26.0 |
| | | | | | | 8 | 8.7 | 19.6 | 27.2 | 13.8 | 28.5 |
| | | | 180 | 50 | 5 | 9 | 26.1 / 28.0 | 45.5 / 46.0 | 6.3 / 6.7 | 7.3 / 7.3 | 14.3 / 11.7 |
| | | | | | | 10 | 23.8 / 28.0 | 41.3 / 48.3 | 10.7 / 5.4 | 6.6 / 7.2 | 16.6 / 11.2 |
| | | | 160 | 125 | 6 | 11 | 7.0 | 23.0 | 10.4 | 36.6 | 22.9 |
| | | | | | | 12 | 7.4 | 23.1 | 10.6 | 35.3 | 23.6 |

Phase seperation was observed with Samples 9 and 10

What is claimed is:

1. In a method where t-butanol is reacted with methanol in a reaction zone in the presence of a catalyst to provide methyl-tert-butyl ether, the improvement of accomplishing the reaction in one-step which comprises using as a catalyst a Y-zeolite selected from the group consisting of:

an ammonium-exchanged, thermally stable Y-zeolite having a Si:Al ratio of ca. 11:1; and a rare-earth exchanged zeolite having a Si:Al ratio of between 1.5:1 and 2:1; and continuously contacting said t-butanol and methanol in a molar amount of about 0.1 to 10 moles of methanol per mole of t-butanol with said catalyst at a temperature of about 80° C. to about 180° C. and a pressure of about atmospheric to about 1000 psig to obtain the methyl-tert-butyl product, wherein at 180² C. the product comprises a two phase mix of an isobutylene-MTBE product-rich phase and a heavier aqueous methanol-rich phase.

* * * * *

UNITED STATES PATENT AND TRADEMARK OFFICE
CERTIFICATE OF CORRECTION

PATENT NO. : 5,214,217
DATED : May 25, 1993
INVENTOR(S) : John Frederick Knifton It is certified that error appears in the above-indentified patent and that said Letters Patent is hereby corrected as shown below:

Claim 1, Col. 14, line 30, please delete "1802 C." and insert therefor --180°C--.

Signed and Sealed this

Fourteenth Day of December, 1993

Attest:

BRUCE LEHMAN

Attesting Officer        Commissioner of Patents and Trademarks